(12) United States Patent
Amin

(10) Patent No.: US 11,890,442 B2
(45) Date of Patent: Feb. 6, 2024

(54) SYSTEMS AND METHODS FOR LOCATING AND IDENTIFYING AN IMPLANTED MEDICAL DEVICE

(71) Applicant: Bard Peripheral Vascular, Inc., Tempe, AZ (US)

(72) Inventor: Murtaza Y. Amin, Farmington, UT (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 751 days.

(21) Appl. No.: 16/961,213

(22) PCT Filed: Jan. 24, 2019

(86) PCT No.: PCT/US2019/015013
§ 371 (c)(1),
(2) Date: Jul. 9, 2020

(87) PCT Pub. No.: WO2019/147857
PCT Pub. Date: Jan. 8, 2019

(65) Prior Publication Data
US 2020/0368513 A1 Nov. 26, 2020

Related U.S. Application Data

(60) Provisional application No. 62/622,555, filed on Jan. 26, 2018.

(51) Int. Cl.
*A61M 39/02* (2006.01)
*A61M 5/142* (2006.01)

(52) U.S. Cl.
CPC .... *A61M 39/0208* (2013.01); *A61M 5/14276* (2013.01); *A61M 2039/0238* (2013.01); *A61M 2205/502* (2013.01); *A61M 2205/60* (2013.01)

(58) Field of Classification Search
None
See application file for complete search history.

(56) References Cited

U.S. PATENT DOCUMENTS

| | | | |
|---|---|---|---|
| 5,061,248 A | 10/1991 | Sacco | |
| 5,342,311 A | 8/1994 | Dirina | |

(Continued)

FOREIGN PATENT DOCUMENTS

| | | | |
|---|---|---|---|
| CN | 1878591 A | 12/2006 | |
| CN | 1899222 A | 1/2007 | |

(Continued)

OTHER PUBLICATIONS

Website: Analog IC Tips, article: How do RFID tags and reader antennas work? https://www.analogictips.com/rfid-tag-and-reader-antennas/ date: May 2, 2017 (Year: 2017).*

(Continued)

*Primary Examiner* — Manuel A Mendez
(74) *Attorney, Agent, or Firm* — Rutan & Tucker LLP

(57) ABSTRACT

Systems and methods for detecting an implanted medical device, such as a vascular access port. The implanted medical device may include at least one passive RFID tag that has disposed thereon information about the implanted medical device. The at least one passive RFID tag is designed to be interrogated by a detector associated with an external device, such as an infusion set with an access needle. The interrogating signal induces a return signal from the at least one passive RFID tags. The strength of the return signal may be dependent on the distance and orientation of the tag relative to the detector. The system may be designed to interpret different signal strengths from different RFID tags to guide the needle to a correct insertion position, thereby accessing a port that cannot be readily detected visually or by palpation.

14 Claims, 6 Drawing Sheets

(56) References Cited

U.S. PATENT DOCUMENTS

| | | |
|---|---|---|
| 5,360,407 A | 11/1994 | Leonard et al. |
| 5,423,334 A | 6/1995 | Jordan |
| 5,460,612 A | 10/1995 | Madore |
| 5,476,460 A | 12/1995 | Montalvo |
| 5,533,979 A | 7/1996 | Nabai et al. |
| 5,620,419 A | 4/1997 | Lui et al. |
| 5,758,667 A | 6/1998 | Slettenmark |
| 5,771,895 A | 6/1998 | Slager |
| 5,797,954 A | 8/1998 | Shaffer et al. |
| 6,654,629 B2 | 11/2003 | Montegrande |
| 6,673,091 B1 | 1/2004 | Shaffer et al. |
| 7,044,932 B2 | 5/2006 | Borchard et al. |
| 7,329,239 B2 | 2/2008 | Safabash et al. |
| 7,621,749 B2 | 11/2009 | Munday |
| 7,632,263 B2 | 12/2009 | Denoth et al. |
| 7,708,730 B2 | 5/2010 | Steinbach et al. |
| 7,762,993 B2 | 7/2010 | Perez |
| 7,794,451 B1 | 9/2010 | Chuter et al. |
| 7,824,371 B2 | 11/2010 | Perez |
| 7,914,510 B2 | 3/2011 | Steinbach et al. |
| 8,171,938 B2 | 5/2012 | Bengtson |
| 8,177,808 B2 | 5/2012 | Mullani |
| 8,192,398 B2 | 6/2012 | Hoendervoogt et al. |
| 8,246,578 B2 | 8/2012 | Matsumoto |
| 8,308,740 B2 | 11/2012 | Tolley et al. |
| 8,475,407 B2 | 7/2013 | Kalpin et al. |
| 8,534,293 B2 | 9/2013 | Bzostek et al. |
| RE44,639 E | 12/2013 | Squitieri |
| 8,715,232 B2 | 5/2014 | Yodfat et al. |
| 8,795,229 B2 | 8/2014 | Bakhtyari-Nejad-Esfahani |
| 8,894,616 B2 | 11/2014 | Harrison et al. |
| 8,926,591 B2 | 1/2015 | Schutz et al. |
| 8,974,422 B2 | 3/2015 | Gill et al. |
| 9,884,150 B2 | 2/2018 | Jho et al. |
| 10,420,884 B2 | 9/2019 | Howell et al. |
| 10,471,205 B2 | 11/2019 | Jho et al. |
| 2002/0022855 A1 | 2/2002 | Bobroff et al. |
| 2002/0067359 A1 | 6/2002 | Brodsky et al. |
| 2002/0072720 A1 | 6/2002 | Hague et al. |
| 2003/0040753 A1 | 2/2003 | Daum et al. |
| 2003/0163096 A1 | 8/2003 | Swenson et al. |
| 2003/0204165 A1 | 10/2003 | Houben et al. |
| 2005/0059884 A1 | 3/2005 | Krag |
| 2005/0101912 A1 | 5/2005 | Faust et al. |
| 2005/0119611 A1 | 6/2005 | Marano-Ford et al. |
| 2005/0154303 A1 | 7/2005 | Walker et al. |
| 2006/0033609 A1 | 2/2006 | Bridgelall |
| 2006/0247584 A1 | 11/2006 | Sheetz et al. |
| 2006/0264898 A1 | 11/2006 | Beasley et al. |
| 2007/0078391 A1 | 4/2007 | Wortley et al. |
| 2007/0191772 A1 | 8/2007 | Wojcik |
| 2007/0238984 A1 | 10/2007 | Maschke et al. |
| 2007/0282196 A1* | 12/2007 | Birk ............... A61F 5/0003 600/424 |
| 2008/0004642 A1 | 1/2008 | Birk et al. |
| 2008/0021313 A1 | 1/2008 | Eidenschink et al. |
| 2008/0083413 A1 | 4/2008 | Forsell |
| 2008/0319414 A1 | 12/2008 | Yodfat et al. |
| 2009/0062744 A1 | 3/2009 | Weilbacher et al. |
| 2009/0082782 A1 | 3/2009 | Kalpin |
| 2009/0093765 A1 | 4/2009 | Glenn |
| 2009/0105688 A1 | 4/2009 | McIntyre et al. |
| 2009/0156928 A1 | 6/2009 | Evans et al. |
| 2009/0227951 A1 | 9/2009 | Powers et al. |
| 2010/0004597 A1 | 1/2010 | Gyrn et al. |
| 2010/0010339 A1 | 1/2010 | Smith et al. |
| 2010/0141454 A1* | 6/2010 | Bantin ............ G01S 13/4454 340/572.1 |
| 2010/0204765 A1 | 8/2010 | Hall et al. |
| 2010/0256594 A1 | 10/2010 | Kimmell et al. |
| 2010/0298704 A1 | 11/2010 | Pelissier et al. |
| 2011/0237935 A1 | 9/2011 | Kalpin et al. |
| 2011/0275930 A1* | 11/2011 | Jho ................. A61M 5/14276 604/288.01 |
| 2012/0172711 A1 | 7/2012 | Kerr et al. |
| 2012/0289819 A1 | 11/2012 | Snow |
| 2013/0218085 A1 | 8/2013 | Knobloch |
| 2014/0039452 A1 | 2/2014 | Bangera et al. |
| 2014/0097303 A1 | 4/2014 | Lake |
| 2014/0207110 A1 | 7/2014 | Jonas |
| 2015/0250944 A1 | 9/2015 | Howell et al. |
| 2017/0100598 A1 | 4/2017 | Gross et al. |
| 2018/0154075 A1 | 6/2018 | Jho et al. |
| 2019/0029760 A1 | 1/2019 | Nahman et al. |
| 2019/0329015 A1 | 10/2019 | Kang |
| 2019/0350672 A1 | 11/2019 | Smith et al. |
| 2019/0351136 A1 | 11/2019 | Howell et al. |
| 2020/0061288 A1 | 2/2020 | Jho et al. |
| 2020/0069929 A1 | 3/2020 | Mason et al. |
| 2021/0402085 A1 | 12/2021 | Howell et al. |

FOREIGN PATENT DOCUMENTS

| | | |
|---|---|---|
| CN | 101066480 A | 11/2007 |
| CN | 101500626 A | 8/2009 |
| CN | 101815550 A | 8/2010 |
| CN | 103327902 A | 9/2013 |
| CN | 103328021 A | 9/2013 |
| JP | H6-296633 A | 10/1994 |
| JP | 2004-283289 A | 10/2004 |
| JP | 2006-102360 A | 4/2006 |
| JP | 2008-539025 A | 11/2008 |
| JP | 2013-531999 | 8/2013 |
| WO | 2006101993 A2 | 9/2006 |
| WO | 2006116438 A2 | 11/2006 |
| WO | 2010015001 A1 | 2/2010 |
| WO | 2011140379 A2 | 11/2011 |
| WO | 2012034085 A1 | 3/2012 |
| WO | 2013152209 A1 | 10/2013 |
| WO | 2014155075 A1 | 10/2014 |
| WO | 2015134766 A1 | 9/2015 |
| WO | 2019147857 A1 | 8/2019 |
| WO | 2022115099 A1 | 6/2022 |

OTHER PUBLICATIONS

CN 201180033387.5 filed Jan. 5, 2013 First Office Action dated Oct. 16, 2014.
CN 201180033387.5 filed Jan. 5, 2013 Second Office Action dated Apr. 13, 2015.
CN 201180033387.5 filed Jan. 5, 2013 Third Office Action dated Sep. 2, 2015.
CN 201610592317.8 filed Jul. 25, 2016 Office Action dated Feb. 24, 2018.
CN 201610592317.8 filed Jul. 25, 2016 Office Action dated Nov. 12, 2018.
JP 2013-509275 filed Oct. 30, 2012 Decision of Rejection dated Sep. 2, 2015.
JP 2013-509275 filed Oct. 30, 2012 First Office Action dated Feb. 6, 2015.
JP 2015-249575 filed Dec. 22, 2015 Decision for Rejection dated May 22, 2017.
JP 2015-249575 filed Dec. 22, 2015 First Office Action dated Oct. 4, 2016.
MX/a/2012/012802 filed Nov. 1, 2012 Office Action dated May 31, 2013.
MX/a/2012/012802 filed Nov. 1, 2012 Office Action dated Nov. 19, 2013.
PCT/US2011/035406 filed May 5, 2011 International Preliminary Report on Patentability dated Feb. 20, 2014.
PCT/US2011/035406 filed May 5, 2011 International Seach Report dated Dec. 16, 2011.
PCT/US2011/035406 filed May 5, 2011 Written Opinion dated Dec. 16, 2011.
PCT/US2019/015013 filed Jan. 24, 2019 International Preliminary Report on Patentability dated Jul. 28, 2020.
PCT/US2019/015013 filed Jan. 24, 2019 International Search Report and Written Opinion dated Jun. 20, 2019.
U.S. Appl. No. 13/101,968, filed May 5, 2011 Decision on Appeal dated Jun. 26, 2017.

(56) References Cited

OTHER PUBLICATIONS

U.S. Appl. No. 13/101,968, filed May 5, 2011 Final Office Action dated Feb. 6, 2015.
U.S. Appl. No. 13/101,968, filed May 5, 2011 Final Office Action dated Oct. 24, 2013.
U.S. Appl. No. 13/101,968, filed May 5, 2011 Non-Final Office Action dated Apr. 24, 2013.
U.S. Appl. No. 13/101,968, filed May 5, 2011 Non-Final Office Action dated Sep. 11, 2014.
U.S. Appl. No. 13/101,968, filed May 5, 2011 Notice of Allowance dated Sep. 20, 2017.
U.S. Appl. No. 15/887,675, filed Feb. 2, 2018 Advisory Action dated Mar. 29, 2019.
U.S. Appl. No. 15/887,675, filed Feb. 2, 2018 Final Office Action dated Jan. 17, 2019.
U.S. Appl. No. 15/887,675, filed Feb. 2, 2018 Non-Final Office Action dated Jun. 14, 2018.
U.S. Appl. No. 15/887,675, filed Feb. 2, 2018 Restriction Requirement dated Apr. 11, 2018.
U.S. Appl. No. 16/672,062, filed Nov. 1, 2019 Final Office Action dated Jan. 19, 2022.
U.S. Appl. No. 16/672,062, filed Nov. 1, 2019 Board Decision dated May 5, 2022.
U.S. Appl. No. 16/672,062, filed Nov. 1, 2019 Non-Final Office Action dated Sep. 20, 2021.
CN 201580012524.5 filed Sep. 7, 2016 Office Action dated Jan. 21, 2019.
EP 15757893.1 filed Aug. 30, 2016 Extended European Search Report dated Dec. 21, 2016.
EP 15757893.1 filed Aug. 30, 2016 Office Action dated Feb. 20, 2019.
PCT/US2015/018999 filed Mar. 5, 2015 Search Report dated Jul. 28, 2015.
PCT/US2020/062076 filed Nov. 24, 2020 International Preliminary Report on Patentability dated Apr. 14, 2023.
PCT/US2020/062076 filed Nov. 24, 2020 International Search Report and Written Opinion dated Aug. 11, 2021.
U.S. Appl. No. 14/639,706, filed Mar. 5, 2015 Final Office Action dated Apr. 27, 2018.
U.S. Appl. No. 14/639,706, filed Mar. 5, 2015 Final Office Action dated Jul. 6, 2017.
U.S. Appl. No. 14/639,706, filed Mar. 5, 2015 Non-Final Office Action dated Dec. 31, 2018.
U.S. Appl. No. 14/639,706, filed Mar. 5, 2015 Non-Final Office Action dated Feb. 17, 2017.
U.S. Appl. No. 14/639,706, filed Mar. 5, 2015 Notice of Allowance dated May 10, 2019.

\* cited by examiner

SYSTEMS AND METHODS FOR LOCATING AND IDENTIFYING AN IMPLANTED MEDICAL DEVICE

PRIORITY

This application is a U.S. national stage from International Patent Application No. PCT/US2019/015013, filed Jan. 24, 2019, which claims the benefit of priority to U.S. Provisional Application No. 62/622,555, filed Jan. 26, 2018, each of which is incorporated by reference in its entirety into this application.

BACKGROUND

Implantable access ports, or simply "ports," such as central venous access ports provide a convenient method to repeatedly deliver a substance to remote areas of the body by way of an attached catheter without utilizing a surgical procedure each time. Ports are implantable within the body and permit the infusion of medicine, parenteral solutions, blood products, or other fluids. Additionally, ports are also used for blood sampling. In common practice, a port is subcutaneously implanted within the body, and a catheter is connected to the port in fluid communication therewith. The catheter is routed to a remote area where a fluid is desired to be delivered or removed. To deliver the fluid, a caregiver locates a septum of the port by palpation of a patient's skin. Port access is accomplished by percutaneously inserting a needle, typically a non-coring needle, through the septum of the port and into a chamber of the port. A fluid containing a drug or some other beneficial substance can then be administered by bolus injection or continuous infusion into the chamber of the port. The fluid then flows through the chamber into the catheter and finally to the remote site where the fluid is desired.

Ports, particularly port septa, can be difficult to find once the ports are implanted under the skin. Further correctly identifying the type of port, make, model and other pertinent data about the device is also important. Accordingly, there is a need to facilitate finding and identifying medical devices such as ports and their septa once such medical devices are implanted. Disclosed herein are at least implantable ports, implantable port-detecting devices, and methods thereof.

SUMMARY

Disclosed herein is an implantable medical device, such as a port, including, in some embodiments, a housing and a septum over the housing. The housing includes a chamber having a major opening to the chamber. The septum is over the major opening of the housing. One or more portions of the implantable port incorporate an RFID tag for locating the septum of the implantable port in vivo by signal reflection and detection of the RFID tag.

In an aspect of the invention, a system for detecting a medical device implanted in a body of a patient, is disclosed, the system includes an implantable medical device, the implantable medical device includes an RFID tag. The system also includes an infusion set, the infusion set includes a needle and a detector. The detector provides an interrogation signal, the interrogation signal induces the RFID tag to provide a return signal.

In an aspect of the invention the detector uses the strength of the return signal to determine a location of the RFID tag relative to the detector. In an aspect of the invention, the detector uses the strength of the return signal to determine an orientation of the RFID tag relative to the detector. In an aspect of the invention, the system further includes a second RFID tag, wherein the detector uses the relative strength of the return signals from each of the first and second RFID tags to determine a location of the port relative to the detector. In an aspect of the invention, the first and second RFID tags are disposed in a co-planar arrangement. In an aspect of the invention, the RFID tag includes information encoded thereon pertaining to the medical device. In an aspect of the invention the information encoded on the RFID tag includes at least one of make of the device, model of the device, device composition, device capabilities, date of manufacture, serial number, and lot number. In an aspect of the invention a user interface device is provided for interpreting and displaying information encoded in the return signal from the RFID tag. In an aspect of the invention. In an aspect of the invention the user interface includes a display for depicting written, numerical, or iconic information about the medical device. In an aspect of the invention, the user interface includes a display for depicting written, numerical, or iconic information about the location and orientation of medical device.

In an aspect of the invention, a method of detecting an implanted medical device is disclosed. The method includes, providing a detector and an implanted medical device, the implanted medical device includes a first RFID tag, emitting a first signal from the detector, the first signal being received by the first RFID tag, which induces a second signal from the first RFID tag, the second signal being received by the detector, deriving a position of the implanted medical device relative to the detector based on the strength of the return signal from the first RFID tag. In an aspect of the invention, the implanted medical device includes a second RFID tag that receives the first signal and induces a third signal from the second RFID tag. In an aspect of the invention, the detector compares the relative strength of the second and third signals to determine a position of the implanted medical device relative to the detector. In an aspect of the invention, a user interface is provided, the user interface interprets and displays information about the implanted medical device. In an aspect of the invention, the detector receives information about the implanted medical device from either of the second and third signals. In an aspect of the invention, the user interface interprets and displays the location of the implanted medical device.

In an aspect of the invention, an apparatus for detecting a vascular access port is provided, the apparatus including a vascular access port, the port including a first RFID tag, an infusion set, the infusion set including a detector and a needle, the needle configured for accessing the port, the detector configured for producing an interrogation signal, the interrogation signal inducing a first return signal from the first RFID tag; and a user interface coupled with the detector configured for receiving and interpreting a first set of information from the first return signal. In an aspect of the invention, the port includes a second RFID tag, the interrogation signal induces a second return signal from the second RFID tag, the user interface receives and interprets a second set of information when both the first and second return signals are received. In an aspect of the invention, the first set of information includes information pertaining to the type of vascular access port. In an aspect of the invention, the information pertaining to the type of vascular access port includes one of the port make, port model, the power injectable capabilities of the port, the MRI compatibility of the port, the number of catheter lumens connected to the port, and the port serial number. In an aspect of the invention, the second set of information includes at least one of the distance, direction and orientation of the port relative to the infusion set.

These and other features of the concepts provided herein will become more apparent to those of skill in the art in view of the accompanying drawings and following description, which disclose particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Figure 1:
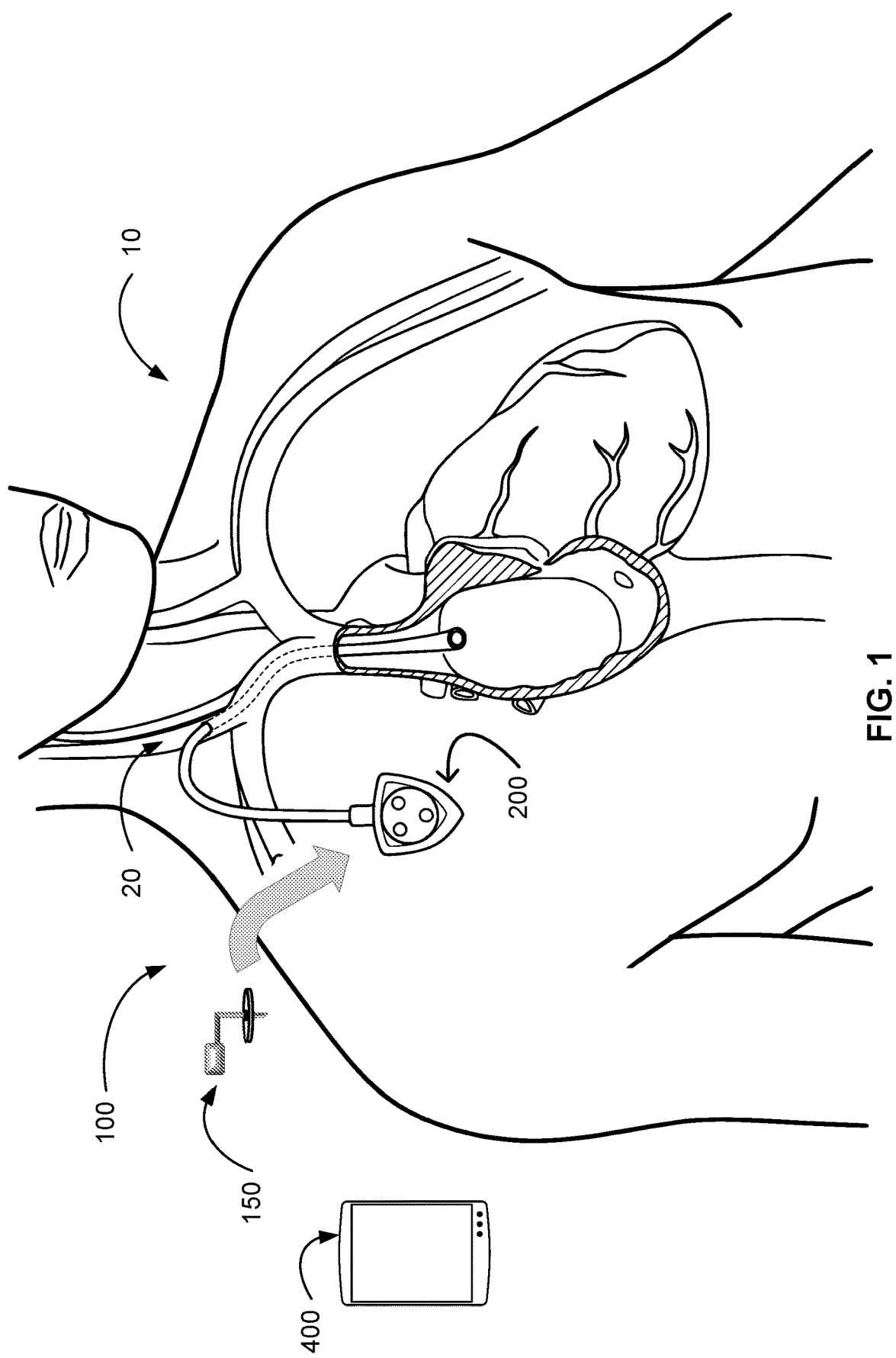
FIG. 1 illustrates an exemplary environment of use for an implantable medical device detection system in accordance with an embodiment of the present invention.

Reference will now be made to figures wherein like structures will be provided with like reference designations. It is understood that the drawings are diagrammatic and schematic representations of exemplary embodiments of the present invention, and are neither limiting nor necessarily drawn to scale. Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. Also, the words "including," "has," and "having," as used herein, including the claims, shall have the same meaning as the word "comprising."

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

Embodiments of the present invention are generally directed to a system configured to locate and identify an implanted medical device disposed within the body of a patient. An example of such a medical device includes an implantable vascular access port, though a variety of other implantable devices can benefit from use of the present system. Ports, particularly port septa, can be difficult to find once the ports are implanted under the skin. Accordingly, there is a need to facilitate finding medical devices such as ports and their septa once such medical devices are implanted. As such, set forth below are various implantable port-detection systems, catheter assemblies including implantable ports, the implantable ports, and implantable port-detecting devices. Methods associated with the foregoing are also set forth below.

Implantable Port-Detection System

FIG. 1 illustrates an exemplary environment of use for the present system 100 for locating and identifying an implanted medical device according to one embodiment. The system 100 includes an infusion set 150, a medical device, such as a vascular access port ("port") 200, a catheter 300, and a user interface 400. As used herein, a port 200 is used as an exemplary medical device, however it will be appreciated that embodiments of the system 100 can also include other implantable medical devices such as catheters, stents, pumps, combinations thereof, or the like. In addition, port 200 is shown throughout the drawings with certain features, such as septum bumps, which are optional. In addition, the port 200 is shown as having a certain shape, which is also optional. It should be appreciated that the locating and identifying system described herein is possible for any type of vascular access port or other implanted medical device. The port 200 is subcutaneously implanted in a patient 10 with a catheter 300 fluidly connecting the port 200 with a vasculature 20 of the patient 10. An infusion set 150 can transcutaneously access the port 200 to deliver medicaments or other fluids to the port 200 and to the vasculature 20 of the patient by way of catheter 300. As used herein, the infusion set 150 can include any infusion set, extension set, or needle device that can be used to fluidly access the implanted port 200 for the delivery of medicaments or other fluids.

Figure 2:
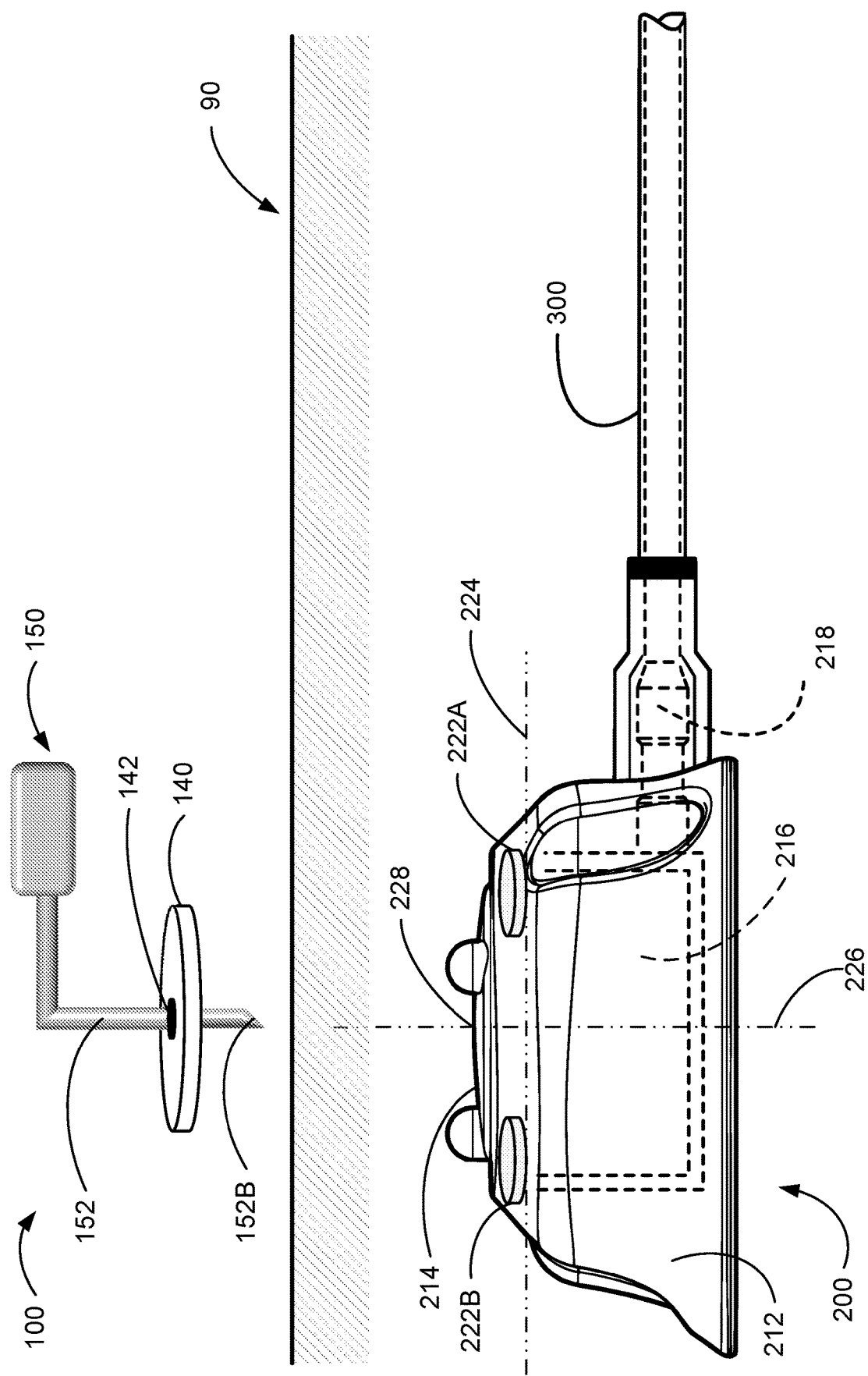
FIG. 2 illustrates a side view of an implantable medical device detection system in accordance with an embodiment of the present invention.
Figure 3:
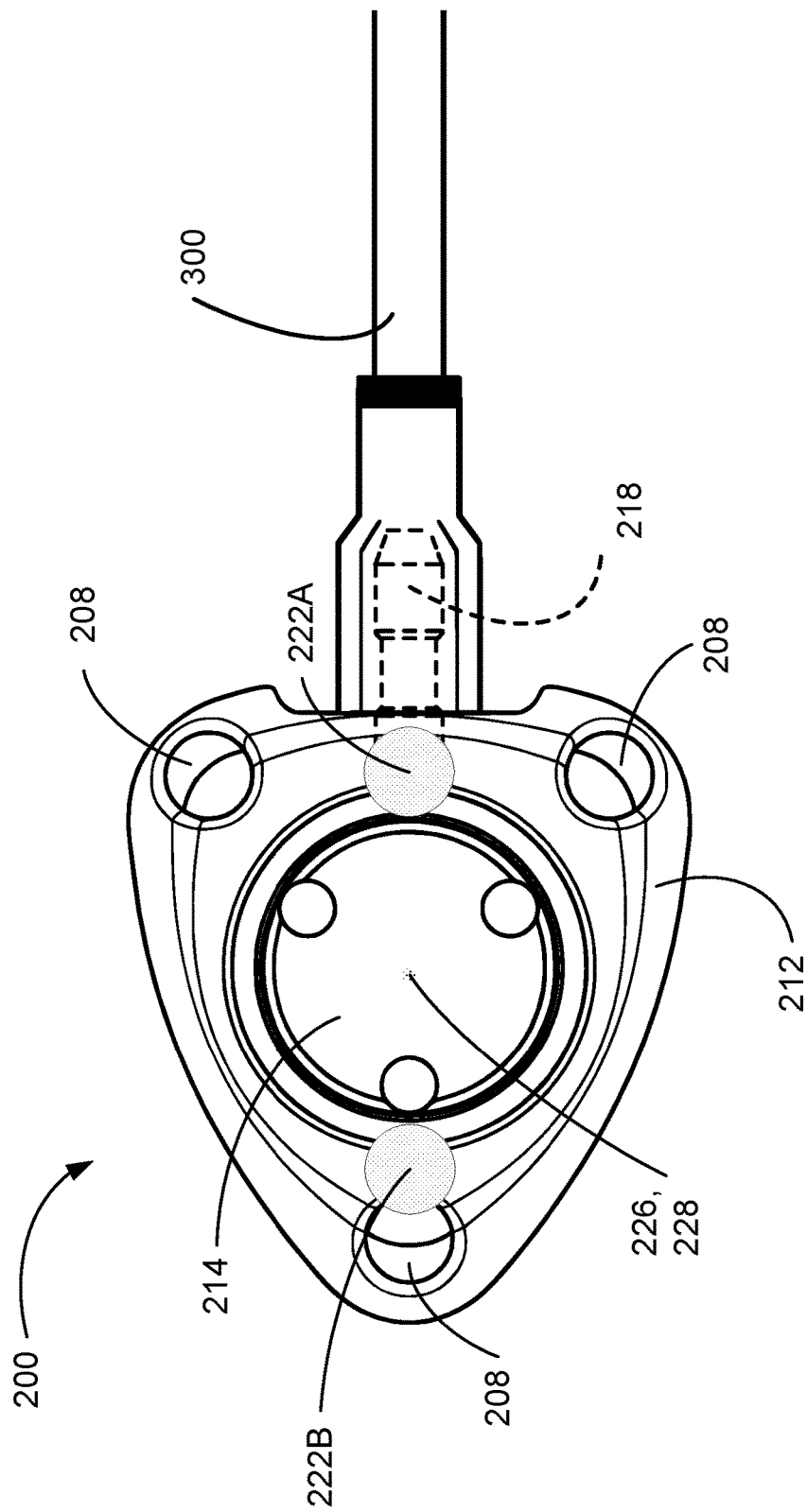
FIG. 3 illustrates a plan view of an implantable medical device detection system in accordance with an embodiment of the present invention.

FIGS. 2-3 illustrate further details of the system 100 for locating and identifying an implanted medical device, according to one embodiment. The port 200 includes a body 212 and a needle-penetrable septum 214 that cooperates with the body 212 to define a fluid reservoir 216. Optionally, the port body 212 can include suture holes 208. An indwelling catheter 300 is fluidly connected to an outlet 218 of the reservoir 216 of the port 200 so as to enable medicaments or other fluids transcutaneously delivered to the port reservoir 216 via a needle 152 of an infusion set 150 (via needle piercing of the septum 214) to be delivered to the vasculature 20 of the patient 10.

The port 200 further includes at least two radiofrequency identification ("RFID") tags 222A and 222B included with the body 212. In an embodiment, the RFID tags 222A, 222B are disposed on an outer surface of the medical port 200 using an adhesive, weld, fasteners, or similar techniques known in the art. In an embodiment, the RFID tags 222A, 222B are integrated within the body 212 of the port 200. In an embodiment, the RFID tags 222A, 222B are disposed in a co-planar arrangement with respect to a substantially horizontal plane 224 that is parallel with a top surface of the septum 214. Further, the RFID tags 222A, 222B are positioned so as to be equidistant from a centerline 226 of the port body 212, which centerline 226 also passes through a centerpoint 228 of the septum 214, as shown in FIG. 1. It will be appreciated that the port 200 can include more than two RFID tags orientated in other positional arrangements and are considered to fall within the scope of the present invention. For example, port 200 can include three or four RFID tags orientated along the plane 224 and are spaced about the port septum centerpoint 228, equidistant from each other as well equidistant from the port septum centerpoint 228.

The RFID tags 222A, 222B in the port 200 enables the system 100 to detect, identify, and locate the position of the port 200 after implantation within the patient. As shown in FIG. 1, the system 100 includes a detector 140 configured to detect the presence of the RFID tags 222A, 222B. The detector 140 is positioned so as to be central to the needle 152, and as such, in the present embodiment the detector 140 includes a central hole 142 through which the needle 152 passes. When access to the port 200 by the infusion set 150 is desired, the detector-equipped infusion set 150 is hovered over the patient's skin 90 in an approximate location at which the implanted port 200 is disposed, similar to that shown in FIG. 2. The system 100 is configured such that the detector can detect the presence of the RFID tags 222A, 222B when hovered over the centerline 226 above the implanted port 200. When this occurs, the system 100 determines that the needle 152 is disposed above the center of the septum 214. Vertically lowering the needle 152 at this point enables the distal end 152B thereof to pierce the skin 90 and pass through the septum 214 to enter the port reservoir 216, as desired. Although only one detector 140 is shown, it will be appreciated that the detector 140 can also include an array of two or more detectors associated with the infusion set 150, as discussed herein. Exemplary detectors can include MIFARE® RFIO-RC522 RFID detectors.

In an embodiment, the RFID tags 222A, 222B can be passive RFID tags that do not require a power source but obtains energy from an interrogating signal, emitted by the detector 140. Advantageously this extends the useful life of the implanted medical device as it is not limited by a finite power source. Exemplary RFID tags can include MIFARE® 13.56 MHz RFID tags. The interrogating signal induces a current in the RFID tag. The induced current is sufficient to allow the tag to process the interrogating signal and provide a return signal that includes information encoded on the RFID tag. In an embodiment, the return signal can contain at least a kilobyte of information. In an embodiment, the detector 140 is configured to detect information encoded in the return signal of the one or more RFID tags 222A, 222B. For example, such information can include make, model, type of the port or components thereof, port body composition, capabilities of the port such as power injectability, MRI compatibility, number of catheter lumens connected, date of manufacture, serial number, lot number, combinations thereof, or the like.

Figure 4:
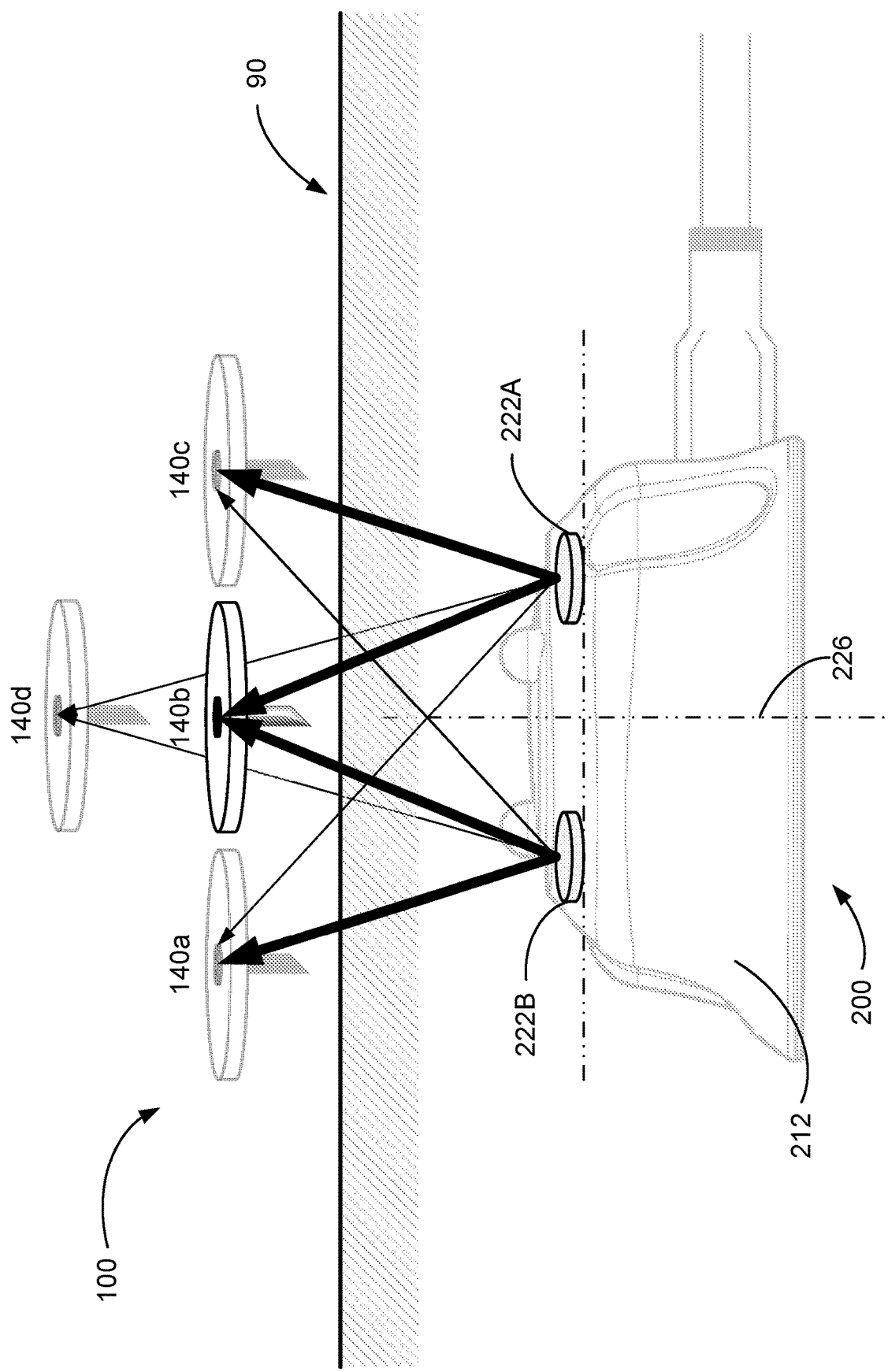
FIG. 4 illustrates a side view of an implantable medical device detection system in accordance with an embodiment of the present invention.

In an embodiment, the return signal from the RFID tag is directional. As such the return signal strength from the RFID tag to the detector decreases quickly when the distance between the RFID tag and the detector increases along the x, y, or z-axes, or when the RFID tag and detector are not co-planar. When the RFID tag and the detector 140 are parallel and co-axially aligned, the return signal is strongest. Accordingly, in a preferred embodiment, two or more RFID tags can be orientated side by side in a port device, orientated in the same plane and have the same normal direction. As such, the detector 140 will determine a center point of the port device when a return signal from both tags is both equal and strongest. For example, FIG. 4 shows four different positions of the detector, 140a-140d, with respect to RFID tags 222A, 222B. At a detector position 140a, the return signal from RFID tag 222A is weaker (lighter arrow) than that from RFID tag 222B (heavier arrow). Conversely, at detector position 140c, the return signal from RFID tag 222B is weaker than that from RFID tag 222A. At detector position 140b, the return signals from both RFID tags 222A, 222B are equal, as such the detector 140 is positioned over the center point. Similarly, a difference in absolute signal strength can indicate differences in distance along a vertical, or z-axis. For example, an equal but relatively weak signal would indicate a that the detector is at a greater vertical distance from the port 200, e.g. detector position 140d, compared to detector position 140b.

As shown in FIGS. 5A-5D, in an embodiment, the system 100 can include a user interface 400 to interpret and communicate the above-described information to a user during operation. The user interface 400 can be integrated with the infusion set 150 or can be a separate device from that of the infusion set 150 and wired or wirelessly coupled thereto. The user interface 400 can include a screen and can depict written, numerical, or iconic information, or combinations thereof, regarding the position of the detector 140 with respect to the implanted port 200. Such information can include distance, direction in three-dimensional space, orientation of the infusion set 150 and port 200 with respect to each other. Such information can be depicted as written instructions, numerical data, iconic, color-coded, or pictorial renderings, or combinations thereof, to display the information. Exemplary user interface devices 400 can include laptops, computer terminals, mobile device, palm top, smartphones, tablets, wearable devices, smartwatches, heads up displays (HUD), Virtual Reality (VR) devices, Augmented Reality (AR) devices, combinations thereof, or the like.

Figure 5A:
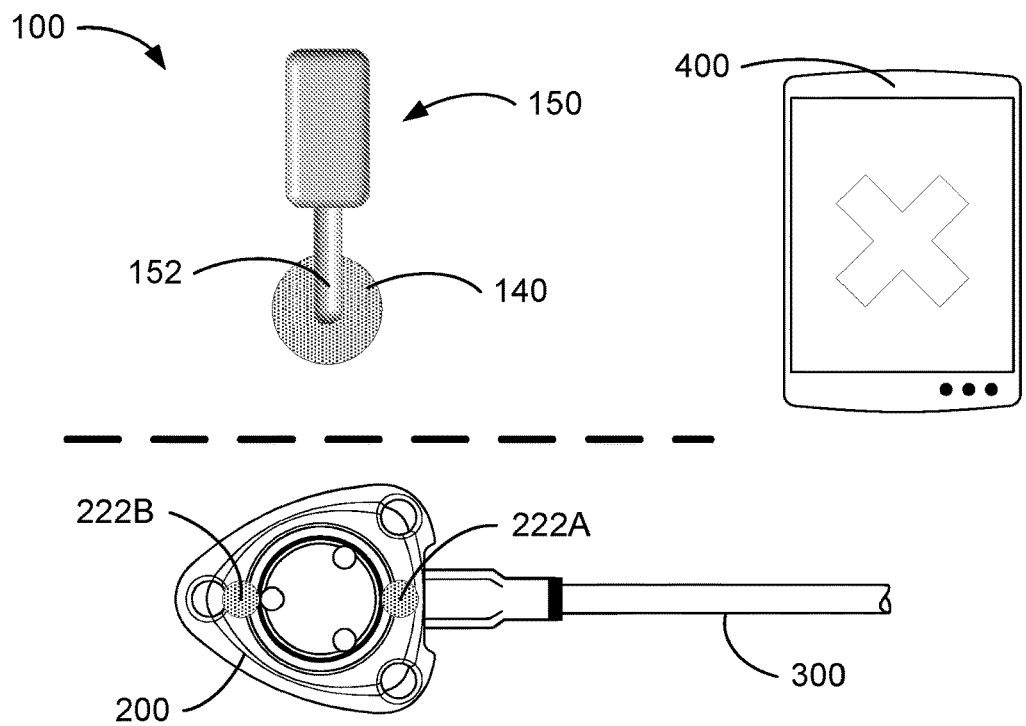
FIGS. 5A-5D illustrates an exemplary method of use of an implantable medical device detection system in accordance with an embodiment of the present invention.
Figure 5B:
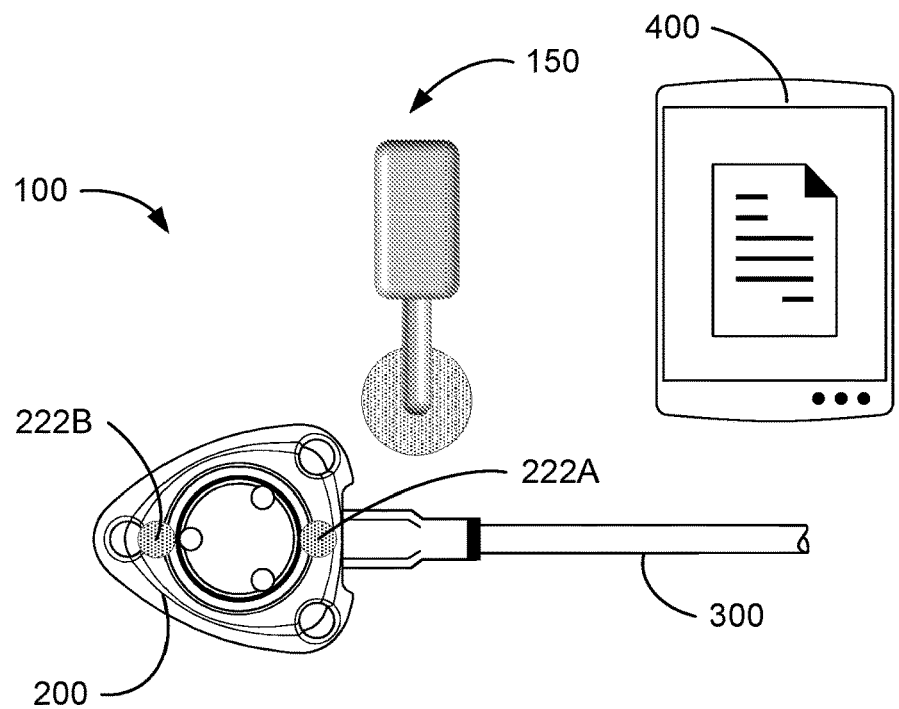
Figure 5C:
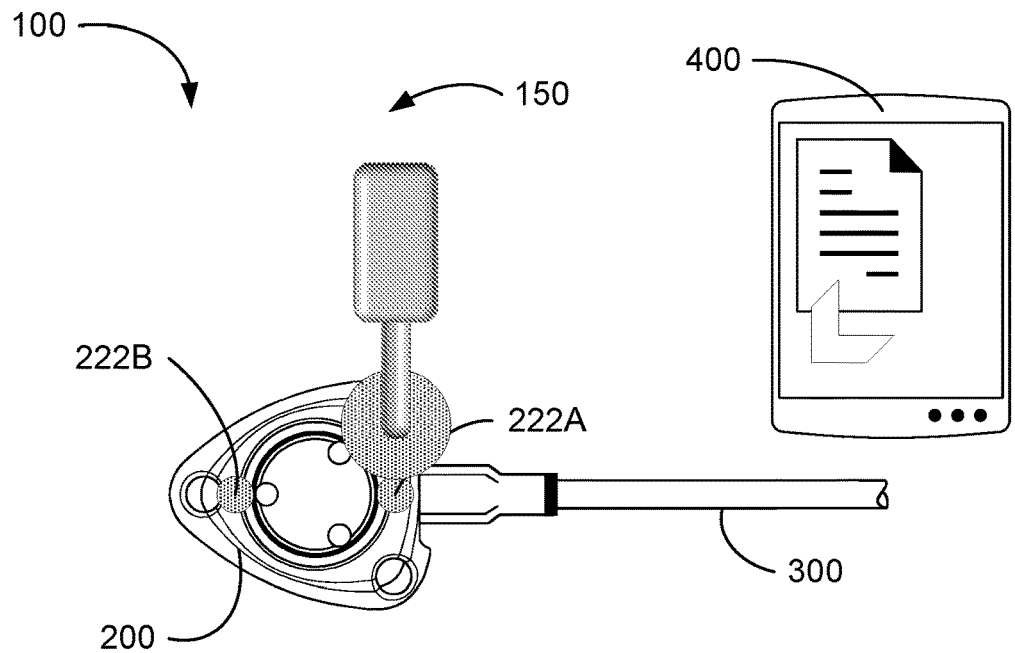
Figure 5D:
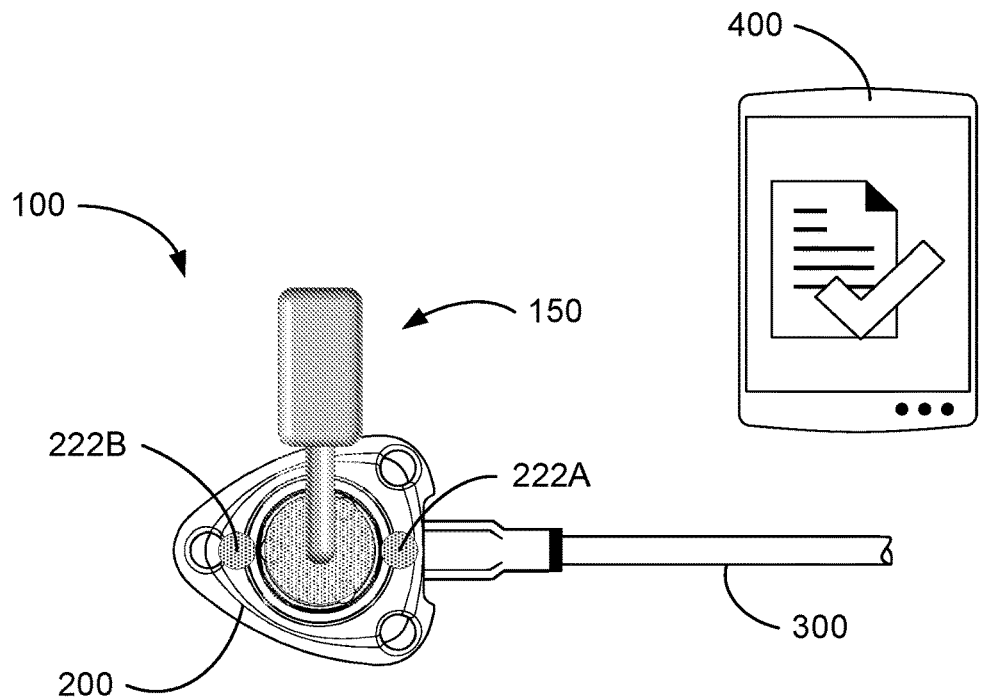

In an exemplary embodiment, as shown in FIG. 5A, when neither RFID tag 222A, 222B is detected, the user interface 400 can depict information indicating that the port is not detected. As shown in FIG. 5B, when the infusion set 150 is within a proximity of only one RFID tag, the user interface 400 can depict information about the port 200, e.g. make, model, serial number, capabilities, etc. As shown in FIG. 5C, when the infusion set 150 is within a proximity two or more of the RFID tags, the user interface 400 can depict both information about the port 200 as well as directional information e.g. direction, distance, orientation, etc. As shown in FIG. 5D, when both RFID tags 222A, 222B are detected and the return signal is both equal and strongest, the user interface 400 can indicate that the infusion set 150 is positioned correctly over the port 200.

While only two RFID tags are shown, it will be appreciated that more than two RFID tags can be used and fall within the scope of the present invention. The system 100 can use the relative position between the detector 140 and the two or more RFID tags 222A, 222B to triangulate an exact position of the needle tip 152B with respect to the septum center point 228 in three dimensional space. In an embodiment, only a single RFID tag can be used, such a system can advantageously be smaller, cheaper and simpler to produce. In an embodiment, if an unknown RFID tag is detected, a message indicating that the tag is unrecognized can be depicted. These and other messages can be employed corresponding to a variety of detection scenarios.

It will be appreciated that the strength of the return signal from the RFID tags 222A, 222B is dependent on the strength of the interrogating signal from the detector 140. Accordingly, the system 100 can vary the strength of the interrogating signal from the detector 140 depending on whether the system is improving detection range or positional accuracy. For example, if one or no tags are detected the interrogation signal can be increased to improve detection range. As two or more tags are detected, the interrogation signal can be reduced to improve positional accuracy.

In an embodiment, detector 140 can include an array of detectors arranged normally to each other. Advantageously, this can improve the accuracy and detection range of the system 100. Moreover, the different orientations of the detectors can identify the orientation of the port 200 relative to the infusion set 150 and/or the patients skin 90. For example, the port may have shifted position or flipped such that the septum is not orientated towards the skin surface. The system 100 can alert a clinician to such problems prior to insertion of the needle even if the port cannot be detected visually or by palpation.

In an exemplary method of use, the implantable medical device, such as port 200, is disposed subcutaneously within the body of a patient such that it cannot be readily detected either visually or by palpitation. The port 200 can include at least one RFID tag 222. An infusion set 150 is provided that includes a detector 140 that is coupled with a user interface device 400. The detector 140 provides an interrogation signal. The interrogation signal can be received by the RFID tag 222 and induces the RFID tag to produce a return signal. The RFID tag can further encode information about the medical device with which it is associated within the return signal. The user interface 400 receives the return signal, by way of the detector 140, and interprets and displays the encoded information about the implanted medical device. Such information can include details about the device, capabilities of the device, combinations thereof, or the like, as discussed herein. The user interface 400 also interprets and displays the position and orientation of the implanted medical device, relative to the detector, based on the relative strength of the return signal compared with the strength of the interrogation signal, the strength of other return signals from different RFID tags, changes thereof over time, and combinations thereof.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

The invention claimed is:

1. A subcutaneous detection system, comprising:
   a vascular access port system, comprising:
      a body enclosing a fluid reservoir, an outlet of the body in communication with the fluid reservoir;
      a needle-penetrable septum covering the fluid reservoir;
      a catheter having a proximal end coupled to the outlet and a distal end including an opening; and
      a RFID tag system, including at least a first RFID tag and a second RFID tag coupled to the body, the first RFID tag and the second RFID tag in a co-planar arrangement; and
   an infusion set, comprising:
      a detector providing an interrogation signal inducing the RFID tag system to provide a return signal; and
      a needle extending through a central hole in the detector.

2. The subcutaneous detection system according to claim 1, wherein the detector uses a strength of the return signal to determine a location of the RFID tag system relative to the detector.

3. The subcutaneous detection system according to claim 1, wherein the detector uses a strength of the return signal to determine an orientation of the RFID tag system relative to the detector.

4. The subcutaneous detection system according to claim 1, wherein the RFID tag system includes information encoded thereon pertaining to the vascular access port system.

5. The subcutaneous detection system according to claim 4, wherein the information encoded on the RFID tag system is selected from the group consisting of make of the vascular access port system, model of the vascular access port system, vascular access port system composition, vascular access port system capabilities, date of manufacture, serial number, lot number, and combinations thereof.

6. The subcutaneous detection system according to claim 1, further comprising a user interface device for interpreting and displaying information encoded in the return signal from the RFID tag system.

7. The subcutaneous detection system according to claim 6, wherein the user interface device includes a display for depicting written, numerical, or iconic information about the vascular access port system.

8. The subcutaneous detection system according to claim 6, wherein the user interface device includes a display for depicting written, numerical, or iconic information about a location and orientation of the vascular access port system.

9. The subcutaneous detection system according to claim 6, wherein the user interface device includes one of a laptop, computer terminal, mobile device, palm top, smartphone, tablet, wearable device, smartwatch, heads up display (HUD), Virtual Reality (VR) device, and Augmented Reality (AR) device.

10. The subcutaneous detection system according to claim 1, wherein the first RFID tag is positioned at a first port location of the vascular access port system, and wherein the second RFID tag is positioned at a second port location of the vascular access port system opposite of the first port location.

11. The subcutaneous detection system according to claim 1, wherein the RFID tag system further comprises a third RFID tag co-planar with the first RFID tag and the second RFID tag, and wherein the first RFID tag is spaced equidistant from the second RFID tag and the third RFID tag.

12. The subcutaneous detection system according to claim 11, wherein the first RFID tag, the second RFID tag, and the third RFID tag are spaced equidistant from a centerpoint of the needle-penetrable septum.

13. The subcutaneous detection system according to claim 1, wherein the RFID tag system further comprises a third RFID tag and a fourth RFID tag, both co-planar with the first RFID tag and the second RFID tag, and wherein the first RFID tag, the second RFID tag, the third RFID tag, and the fourth RFID tag are spaced equidistant about the vascular access port system.

14. The subcutaneous detection system according to claim 13, wherein the first RFID tag, the second RFID tag, the third RFID tag, and the fourth RFID tag are spaced equidistant from a centerpoint of the needle-penetrable septum.

\* \* \* \* \*